United States Patent [19]

Lin et al.

[11] Patent Number: 5,507,843
[45] Date of Patent: Apr. 16, 1996

[54] FUEL COMPOSITIONS

[75] Inventors: Jiang-Jen Lin; Pen-Chung Wang; Sarah L. Weaver, all of Houston, Tex.

[73] Assignee: Shell Oil Company, Houston, Tex.

[21] Appl. No.: 308,715

[22] Filed: Sep. 19, 1994

[51] Int. Cl.$^6$ .................... C10L 1/18; C10L 1/22
[52] U.S. Cl. .................... 44/329; 44/333; 44/340; 44/347; 44/353; 540/362; 540/451; 540/482; 540/531; 546/216; 546/219; 548/520; 548/547
[58] Field of Search ................... 540/362, 482, 540/451, 531; 546/216, 219; 548/520, 547; 44/329, 333, 340, 347, 353, 443, 412, 418, 432

[56] References Cited

U.S. PATENT DOCUMENTS

| | | |
|---|---|---|
| 3,438,757 | 4/1969 | Honnen et al. . |
| 3,574,576 | 4/1971 | Honnen et al. . |
| 3,753,670 | 8/1973 | Strang et al. . |
| 3,756,793 | 9/1973 | Robinson . |
| 4,160,648 | 7/1979 | Lewis et al. . |
| 4,191,537 | 3/1980 | Lewis et al. . |
| 4,231,759 | 11/1980 | Udelhofen et al. . |
| 4,236,020 | 11/1980 | Lewis et al. . |
| 4,270,930 | 6/1981 | Campbell et al. . |
| 4,288,612 | 9/1981 | Lewis et al. . |
| 4,612,335 | 9/1986 | Cuscurida et al. . |
| 4,713,463 | 12/1987 | Chaudhuri et al. . |
| 4,801,400 | 1/1989 | Login et al. ............... 252/357 |
| 4,810,261 | 3/1989 | Sung et al. . |
| 4,830,851 | 5/1989 | Tracy et al. ............... 252/106 X |
| 4,852,993 | 8/1989 | Sung et al. . |
| 4,881,945 | 11/1989 | Buckley, III . |
| 4,883,826 | 11/1989 | Marugg et al. . |
| 4,936,868 | 6/1990 | Johnson . |
| 4,968,321 | 11/1990 | Sung et al. . |
| 4,973,414 | 11/1990 | Nerger et al. . |
| 4,985,047 | 1/1991 | Sung et al. . |
| 5,061,291 | 10/1991 | Sung . |
| 5,123,932 | 6/1992 | Rath et al. . |
| 5,147,414 | 9/1992 | Powers, III et al. . |

*Primary Examiner*—Stephen Kalafut
*Assistant Examiner*—Cephia D. Toomer

[57] ABSTRACT

The present invention is directed to the use of multiple cyclic nitrogen-containing alkoxylate compounds as additives in fuel compositions. The invention is also directed to the use of these multiple cyclic nitrogen-containing alkoxylate compounds for decreasing intake valve deposits, controlling octane requirement increases and reducing octane requirement. The invention is further directed to a class of multiple cyclic nitrogen-containing alkoxylate compounds.

33 Claims, No Drawings

FUEL COMPOSITIONS

BACKGROUND OF THE INVENTION

1. Field of the Invention

The present invention relates to the use of multiple cyclic nitrogen-containing polyether alcohol compounds as additives in fuel compositions and the use of these compounds to decrease intake valve deposits, control octane requirement increases and reduce octane requirement. The present invention further relates to several classes of multiple cyclic nitrogen-containing polyether alcohol compounds.

2. Background

The accumulation of deposits on intake valves of internal combustion engines presents a variety of problems. The accumulation of such deposits is characterized by overall poor driveability including hard starting, stalls, and stumbles during acceleration and rough engine idle.

Many additives are known which can be added to hydrocarbon fuels to prevent or reduce deposit formation, or remove or modify formed deposits, in the combustion chamber and on adjacent surfaces such as intake valves, ports, and spark plugs, which in turn causes a decrease in octane requirement.

Continued improvements in the design of internal combustion engines, e.g., fuel injection and carburetor engines, bring changes to the environment of such engines thereby creating a continuing need for new additives to control the problem of inlet system deposits and to improve driveability which is usually related to deposits.

It would be an advantage to have fuel compositions which would reduce the formation of deposits and modify existing deposits that are related to octane requirement increase and poor driveability in modern engines which burn hydrocarbon fuels.

SUMMARY OF THE INVENTION

The present invention is directed to the use of multiple cyclic nitrogen-containing polyether alcohol compounds as additives in fuel compositions comprising a major amount of a mixture of hydrocarbons in the gasoline boiling range and a minor amount of one or more multiple cyclic nitrogen-containing polyether alcohol compounds of Formula I:

$$R_1-(CH_2-CH-O)_x-(CH_2-CH-O)_y-H \quad \text{(I)}$$
$$\phantom{R_1-(CH_2-CH}|\phantom{O)_x-(CH_2-CH}| $$
$$\phantom{R_1-(CH_2-CH-O)_xx}R_2\phantom{-(CH_2-CH-O}R_3$$

wherein $R_1$ is selected from the group consisting of aklyl of 1 to 100 carbon atoms, alkyl-phenols wherein the alkyl group contains from 1 to 100 carbon atoms; cyclic imides of Formula II:

$$\text{(II)}$$

$$\begin{array}{c} O \\ \| \\ C \\ / \, \backslash \\ (CH_2)_z \quad N- \\ \backslash \, / \\ C \\ \| \\ O \end{array}$$

wherein z is from 2 to 20; cyclic amides of Formula III:

$$\text{(III)}$$

$$\begin{array}{c} O \\ \| \\ C \\ / \, \backslash \\ (CH_2)_a \quad N-, \\ \underline{\phantom{xxxx}} \end{array}$$

wherein a is from 2 to 20; and cyclic compounds of Formula IV:

$$\begin{array}{c} R_4-CH_2 \\ \phantom{R_4-}\backslash \\ \phantom{R_4-CH_2}CH-O- \\ \phantom{R_4-}/ \\ R_5-CH_2 \end{array} \quad \text{(IV)}$$

wherein $R_4$ and $R_5$ are each independently selected from cyclic imides of Formula II:

$$\text{(II)}$$

$$\begin{array}{c} O \\ \| \\ C \\ / \, \backslash \\ (CH_2)_z \quad N-, \\ \backslash \, / \\ C \\ \| \\ O \end{array}$$

wherein z is from 2 to 20; and cyclic amides of Formula III:

$$\text{(III)}$$

$$\begin{array}{c} O \\ \| \\ C \\ / \, \backslash \\ (CH_2)_a \quad N-, \\ \underline{\phantom{xxxx}} \end{array}$$

wherein a is from 2 to 20; $R_2$ and $R_3$ are each individually selected from the group consisting of hydrogen, alkyl of 1 to 100 carbon atoms, cyclic imides of Formula V:

$$\text{(V)}$$

$$\begin{array}{c} O \\ \| \\ C \\ / \, \backslash \\ (CH_2)_b \quad N-(CH_2-CH-O)_c-CH_2- \\ \backslash \, / \phantom{xxxxxxxxxx} | \\ C \phantom{xxxxxxxxxxxx} R_6 \\ \| \\ O \end{array}$$

wherein b is from 2 to 20, each $R_6$ is individually selected from the group consisting of hydrogen and alkyl of 1 to 100 carbon atoms and c is from 0 to 50; and cyclic amides of Formula VI:

$$\text{(VI)}$$

$$\begin{array}{c} O \\ \| \\ C \\ / \, \backslash \\ (CH_2)_d \quad N-(CH_2-CH-O)_e-CH_2- \\ \underline{\phantom{xxxxxx}} \phantom{xxxxxx} | \\ \phantom{xxxxxxxxxxxxxxx} R_7 \end{array}$$

wherein d is from 2 to 20, each $R_7$ is individually selected from the group consisting of hydrogen and alkyl of 1 to 100 carbon atoms and e is from 0 to 50; x and y are each individually from 1 to 50; and the weight average molecular weight of the additive compound is greater than about 600; with the proviso that at least one of $R_1$, $R_2$ and $R_3$ must be a cyclic amide, a cyclic imide or a cyclic compound containing cyclic amides, cyclic imides or a mixture thereof; with the further proviso that $R_1$ must be a cyclic amide of Formula IV when $R_2$ and $R_3$ are hydrogen or alkyl; and with the still further proviso that when only $R_2$ is a cyclic amide or a cyclic imide, x must be greater than one; and with the even still further proviso that when only $R_3$ is a cyclic amide or a cyclic imide, y must be greater than one.

The invention is also directed to the use of these multiple cyclic nitrogen-containing alkoxylate compounds for decreasing intake valve deposits, controlling octane requirement increases and reducing octane requirement. The invention is still further directed to several classes of multiple cyclic nitrogen-containing alkoxylate compounds.

DESCRIPTION OF THE PREFERRED EMBODIMENTS

COMPOUNDS

The compounds of the present invention, broadly expressed as multiple cyclic nitrogen-containing alkoxylates, are a new class of additives useful for hydrocarbon fuels, e.g., fuels in the gasoline boiling range, for preventing deposits in engines, while also decomposing during combustion to environmentally acceptable products. The compounds are also proposed for controlling octane requirement increases and reducing octane requirement. The compounds produce very little residue and are miscible with carriers and other detergents. Non-limiting illustrative embodiments of the compounds useful as additives in the instant invention include those of Formula I:

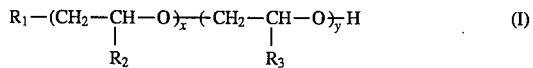

In Formula I, $R_1$ is selected from the group consisting of aklyl of 1 to 100 carbon atoms, alkyl-phenol of 1 to 100 carbon atoms, cyclic imides of Formula II:

wherein z is from 2 to 20; cyclic amides of Formula III:

wherein a is from 2 to 20; and cyclic compounds of Formula IV:

wherein $R_4$ and $R_5$ are each independently selected from cyclic imides of Formula II and cyclic amides of Formula III.

When $R_1$ is alkyl of 1 to 100 carbon atoms, $R_1$ is preferably alkyl of 1 to 50 carbon atoms, more preferably of 1 to 20 carbon atoms, and even more preferably of 1 to 10 carbon atoms.

$R_1$ can also be an alkyl-phenol wherein the alkyl contains from 1 to 100 carbon atoms. Preferably the alkyl of the alkyl-phenol will contain from 1 to 50 carbon atoms and more preferably from 1 to 20 carbon atoms. Particularly preferred compounds are those in which when $R_1$ is alkylphenol, $R_1$ will be nonyl-phenol or dodecyl-phenol.

$R_1$ can also be cyclic imide of Formula II:

wherein z is from 2 to 20. Preferably, z is from 2 to 11, more preferably from 2 to 5, with the most preferred values of z being 2 and 3.

$R_1$ can also be cyclic amide of Formula III:

wherein a is from 2 to 20. Preferably a is from 3 to 11, more preferably from 3 to 5, with the most preferred values of a being 3 and 5.

In addition, $R_1$ can also be the cyclic compound of Formula IV:

wherein $R_4$ and $R_5$ are each independently selected from cyclic imides of Formula II:

wherein z is as defined hereinbefore and cyclic amides of Formula III:

wherein a is as defined hereinbefore. When $R_1$ is cyclic amide of formula IV, $R_4$ and $R_5$ may be the same or different. For instance, one of $R_4$ and $R_5$ can be cyclic imide of Formula II while the other is cyclic amide of Formula III. In an alternative embodiment, $R_4$ and $R_5$ can both be cyclic imide of Formula II or both can be cyclic amide of Formula III. In addition, when $R_4$ and $R_5$ are of the same formula (i.e., both of Formula III), the value of the variable can also be the same or different (i.e., a is 5 for $R_4$ and a is 3 for $R_5$).

Particularly preferred compounds are those in which when $R_1$ is a cyclic compound of Formula IV, $R_4$ and $R_5$ are each cyclic amide of Formula III and each a is 3 or each a is 5; or $R_4$ and $R_5$ are each cyclic imide of Formula II and z is 2. Additional particularly preferred compounds are those in which when $R_1$ is a cyclic compound of Formula IV, $R_4$ is a cyclic imide of Formula II in which the value of z is 2 and $R_5$ is a cyclic amide of Formula III in which the value of a is 3; or in the alternative, $R_4$ is a cyclic imide of Formula II in which the value of z is 2 or 3 and $R_5$ is a cyclic amide of Formula III in which the value of a is 5.

$R_2$ and $R_3$ are each individually selected from the group consisting of hydrogen, alkyl of 1 to 100 carbon atoms, cyclic imides of Formula V:

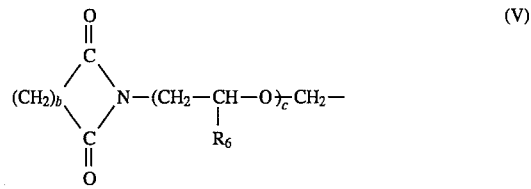

wherein b is from 2 to 20, each $R_6$ is individually selected from the group consisting of hydrogen and alkyl of 1 to 100 carbon atoms and c is from 0 to 50, and cyclic amides of the Formula VI:

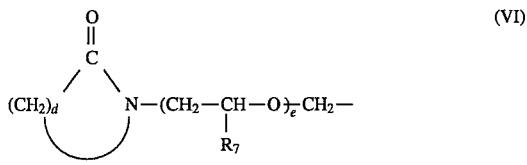

wherein d is from 2 to 20, each $R_7$ is individually selected from the group consisting of hydrogen and alkyl of 1 to 100 carbon atoms and e is from 0 to 50.

$R_2$ and/or $R_3$ may be alkyl of 1 to 100 carbon atoms. When $R_2$ and/or $R_3$ are alkyl, they are preferably alkyl of 1 to 48 carbon atoms, even more preferably alkyl of 1 to 18 carbon atoms. In the more preferred embodiments, when $R_2$ and/or $R_3$ are alkyl, they are alkyl of 1 to 2 carbon atoms, even more preferably, alkyl of 2 carbon atoms.

$R_2$ and/or $R_3$ may also be cyclic imide of Formula V. In Formula V, b is preferably from 2 to 11, more preferably from 2 to 5, with 2 and 3 being the most preferred values of b. Each $R_6$ is preferably individually selected from the group consisting of hydrogen and alkyl of 1 to 50 carbon atoms. When $R_6$ is alkyl, it is even more preferably alkyl of 1 to 20 carbon atoms and most preferably of 8 to 16 carbon atoms. In the more preferred embodiments when $R_2$ and/or $R_3$ are cyclic imide of Formula V, each $R_6$ will individually be selected from hydrogen and alkyl of 1 to 2 carbon atoms and in the most preferred embodiments, each $R_6$ will be individually selected from hydrogen and alkyl of 2 carbon atoms.

In Formula V, c is from 0 to 50, preferably from 0 to 40, more preferably from 0 to 24 and most preferably from 0 to 10. Those of ordinary skill in the art will recognize that when the compounds of Formula I which contain cyclic imides of Formula V are utilized in a composition, c will not have a fixed value but will instead be represented by a range of different values. As used in this specification, c is considered to be a (number) average of the various values of c that are found in a given composition, which number has been rounded to the nearest integer. The range of c was determined by gel permeation chromatography (GPC) analysis in the various examples and is indicated in the various examples by the polydispersity (polydispersity=molecular weight based on the weight average divided by the molecular weight based on the number average).

When c is greater than 1, the individual parenthetical groups are the same or different. For example, if c is 20, all of the parenthetical groups will be the same when each $R_6$ is hydrogen. Alternatively, the parenthetical groups can differ for instance when the $R_6$'s are each individually selected from hydrogen and alkyl from one to four carbon atoms. When the $R_6$'s differ, the parenthetical groups may be present in blocks, i.e., all c groups in which $R_6$ is alkyl of three carbon atoms will be adjacent, followed by all c groups in which $R_6$ is hydrogen, followed by all c groups in which $R_6$ is alkyl of two carbon atoms. When the $R_6$'s differ, they may also be present in any random distribution.

In one preferred embodiment when $R_2$ and/or $R_3$ are cyclic imides of Formula V, c is 0 and in the alternative preferred embodiment, c is 1.

$R_2$ and/or $R_3$ may also be cyclic amide of Formula VI. In Formula VI, d is preferably from 3 to 11, more preferably from 3 to 5, with 3 and 5 being the most preferred values of d. Each $R_7$ is preferably individually selected from the group consisting of hydrogen and alkyl of 1 to 50 carbon atoms. When $R_7$ is alkyl, it is even more preferably alkyl of 1 to 20 carbon atoms and most preferably from alkyl of 8 to 16 carbon atoms. In the more preferred embodiments when $R_2$ and/or $R_3$ are cyclic amide of Formula VI, each $R_7$ will individually be selected from hydrogen and alkyl of 1 to 2 carbon atoms and in the most preferred embodiments, each $R_7$ will be individually selected from hydrogen and alkyl of 2 carbon atoms.

In Formula VI, e is from 0 to 50, preferably from 0 to 40, more preferably from 0 to 24 and even more preferably from 0 to 10. Those of ordinary skill in the art will recognize that when the compounds of Formula I which contain cyclic amides of Formula VI are utilized in a composition, e will not have a fixed value but will instead be represented by a range of different values. As used in this specification, e is considered to be a (number) average of the various values of e that are found in a given composition, which number has been rounded to the nearest integer. The range of e was determined by gel permeation chromatography (GPC) analysis in the various examples and is indicated in the various examples by the polydispersity (polydispersity= molecular weight based on the weight average divided by the molecular weight based on the number average).

When e is greater than 1, the individual parenthetical groups are the same or different. For example, if e is 20, all of the parenthetical groups will be the same when each $R_7$ is hydrogen. Alternatively, the parenthetical groups can differ for instance when the $R_7$'s are each individually selected from hydrogen and alkyl from one to four carbon atoms. When the $R_7$'s differ, the parenthetical groups may be present in blocks, i.e., all e groups in which $R_7$ is alkyl of three carbon atoms will be adjacent, followed by all e groups in which $R_7$ is hydrogen, followed by all e groups in which $R_7$ is alkyl of two carbon atoms. When the $R_7$'s differ, they may also be present in any random distribution.

In one preferred embodiment when $R_2$ and/or $R_3$ are cyclic amides of Formula VI, e is 0 and in the alternative preferred embodiment, e is 1.

While $R_2$ and $R_3$ may individually be selected from the same group (i.e., each $R_2$ and $R_3$ are individually selected from hydrogen and a variety of alkyls), in some instances $R_2$ will be selected from a completely different group than $R_3$ (i.e., each $R_2$ is individually selected from hydrogen and a variety of alkyls while each $R_3$ is individually selected from a variety of cyclic imides of Formula V).

At least one of $R_1$, $R_2$ and $R_3$ must contain a cyclic amide or a cyclic imide. When $R_2$ and $R_3$ are selected from the group consisting of hydrogen and alkyl of 1 to 100 carbon atoms, $R_1$ must be the cyclic compound of Formula IV which contains either two cyclic imides, two cyclic amides or a mixture of a cyclic amide and a cyclic imide.

In Formula I above, x is from 1 to 50, preferably from 1 to 40, more preferably from 1 to 26 and even more preferably from 1 to 13. Those of ordinary skill in the art will recognize that when the compounds of Formula I are used in a composition, x will not have a fixed value but will instead be represented by a range of different values. As used in this specification, x is considered to be a (number) average of the various values of x that are found in a given composition, which number has been rounded to the nearest integer. The range of x was determined by gel permeation chromatography (GPC) analysis in the various examples and is indicated in the various examples by the polydispersity (polydispersity=molecular weight based on the weight average divided by the molecular weight based on the number average).

When x is greater than 1, the individual $R_2$'s are the same or different. For example, if x is 20, each $R_2$ can be alkyl of four carbon atoms. Alternatively, the $R_2$'s can differ and for instance, independently be alkyl from two to four carbon atoms. When the $R_2$'s differ, they may be present in blocks, i.e., all x groups in which $R_2$ is alkyl of three carbon atoms will be adjacent, followed by all 2 groups in which $R_2$ is alkyl of two carbon atoms, followed by all x groups in which $R_2$ is alkyl of four carbon atoms. When the $R_2$'s differ, they may also be present in any random distribution.

In Formula I above, y is from 1 to 50, preferably from 1 to 40, more preferably from 1 to 26 and even more preferably from 1 to 13. Those of ordinary skill in the art will recognize that when the compounds of Formula I are used in a composition, y will not have a fixed value but will instead be represented by a range of different values. As used in this specification, y is considered to be a (number) average of the various values of y that are found in a given composition, which number has been rounded to the nearest integer. The range of y was determined by gel permeation chromatography (GPC) analysis in the various examples and is indicated in the various examples by the polydispersity (polydispersity=molecular weight based on the weight average divided by the molecular weight based on the number average).

When y is greater than 1, the individual $R_3$'s are the same or different. For example, if y is 20, each $R_3$ can be alkyl of four carbon atoms. Alternatively, the $R_3$'s can differ and for instance, independently be alkyl from two to four carbon atoms. When the $R_3$'s differ, they may be present in blocks, i.e., all y groups in which $R_3$ is alkyl of three carbon atoms will be adjacent, followed by all y groups in which $R_3$ is alkyl of two carbon atoms, followed by all y groups in which $R_3$ is alkyl of four carbon atoms. When the $R_3$'s differ, they may also be present in any random distribution.

In one preferred embodiment, $R_1$ is a cyclic compound of Formula IV and $R_2$ and $R_3$ are selected from hydrogen and alkyl of 1 to 2 carbon atoms. In this embodiment, preferably the sum of the values of x and y will not exceed 40, even more preferably, the sum of the values of x and y will not exceed 26. In an alternative preferred embodiment, $R_1$ is selected from cyclic imides of Formula II and cyclic amides of Formula III and $R_2$ and $R_3$ are selected from hydrogen, alkyl of 1 to 2 carbon atoms, cyclic imides of Formula V and cyclic amides of Formula VI with the proviso that at least one of $R_2$ and $R_3$ must be cyclic imide of Formula V or cyclic amide of Formula VI. In this second preferred embodiment, preferably the sum of the values of x and y will not exceed 40, even more preferably, the sum of the values of x and y will not exceed 26. In a still third preferred embodiment, $R_1$ is selected from alkyl-phenols and $R_2$ and $R_3$ are selected from hydrogen, alkyl of 1 to 2 carbon atoms, cyclic imides of Formula V and cyclic amides of Formula VI with the proviso that at least one of $R_2$ and $R_3$ must be cyclic imide of Formula V or cyclic amide of Formula VI. In this third preferred embodiment, preferably the sum of the values of x and y will not exceed 40, even more preferably, the sum of the values of x and y will not exceed 26.

When $R_1$ and $R_3$ are not cyclic imides, cyclic amides or cyclic compounds containing cyclic imides, cyclic amides or mixtures thereof, $R_2$ must be either cyclic imide of Formula V or the cyclic amide of Formula VI. In those embodiments in which $R_2$ is the only cyclic imide or the only cyclic amide, the value of x must be greater than 1.

When $R_1$ and $R_2$ are not cyclic imides, cyclic amides or cyclic compounds containing cyclic imides, cyclic amides or mixtures thereof, $R_3$ must be either cyclic imide of Formula V or the cyclic amide of Formula VI. In those embodiments in which $R_3$ is the only cyclic imide or the only cyclic amide, the value of y must be greater than 1.

Of the compounds of Formula I, the following classes of compounds are novel. In one class of compounds, the compounds are defined by the following formula:

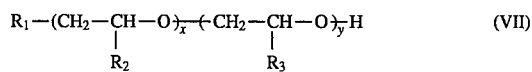

$$R_1-(CH_2-\underset{R_2}{CH}-O)_{\overline{x}}(CH_2-\underset{R_3}{CH}-O)_{\overline{y}}H \qquad (VII)$$

wherein $R_1$ is selected from the group consisting of aklyl of 1 to 100 carbon atoms; cyclic imides of Formula II as defined hereinbefore; cyclic amides of Formula III as defined hereinbefore; and cyclic compounds of Formula IV as defined hereinbefore; and $R_2$ and $R_3$ are each as defined hereinbefore; x and y are each as defined hereinbefore; with the proviso that at least one of $R_1$, $R_2$ and $R_3$ must be a cyclic amide, a cyclic imide or a cyclic compound containing cyclic amides, cyclic imides or a mixture thereof; with the further proviso that $R_1$ must be a cyclic amide of Formula IV when $R_2$ and $R_5$ are hydrogen or alkyl; and with the still further proviso that when only $R_2$ is a cyclic amide or a cyclic imide, x must be greater than one; and with the even still further proviso that when only $R_3$ is a cyclic amide or a cyclic imide, y must be greater than one.

The compounds of Formula I have a weight average molecular weight of at least 600. Preferably, the weight average molecular weight is from about 800 to about 4000, even more preferably from about 800 to about 2000.

Typical compounds represented by Formula I include those listed by structure in Table 1. For purposes of clarity the hydrogens have been eliminated from the ring structures and the standard schematic structure for a benzene ring (without hydrogen and carbon atoms) has been used.

| Example # | Product |
|---|---|
| 1 | 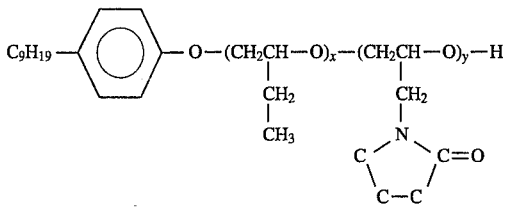<br>wherein x is from 1 to 26 and y is from 1 to 26. |
| 2 | 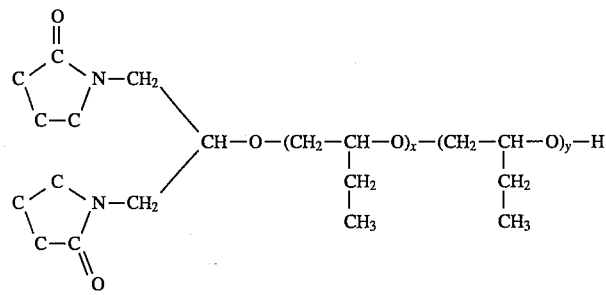<br>wherein x is from 1 to 26 and y is from 1 to 26. |
| 3 | 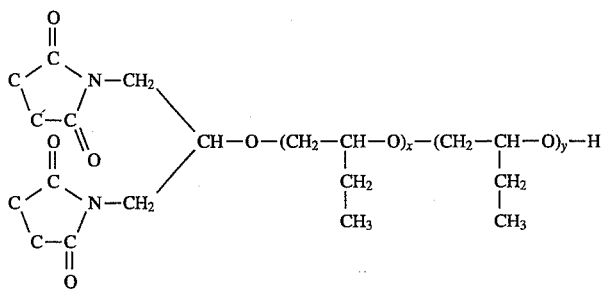<br>wherein x is from 1 to 26 and y is from 1 to 26. |
| 4 | 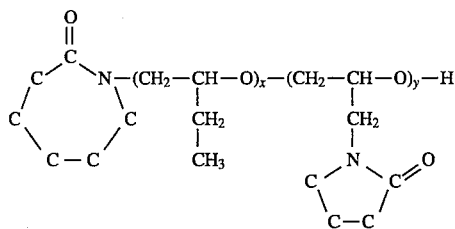<br>wherein x is from 1 to 26 and y is from 1 to 26. |

The compounds of Formula I are illustratively prepared by alkoxylation, i.e., reacting an initiator with one or more epoxides in the presence of a potassium compound. The initiators are selected from cyclic amides, cyclic imides, cyclic amidoalcohols and N-nonylphenol.

In one embodiment of the present invention, the compounds of Formula I are prepared by reacting cyclic imide initiators of Formula VIII:

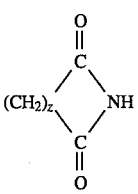 (VIII)

wherein z is as defined hereinbefore, with one or more epoxides. Non-limiting examples of cyclic imides which can be employed include succinimide (available commercially from Mallinckrodt) and glutarimide (available commercially from Morton Thiokol Inc., Afla Products Division), with succinimide being the most preferred.

In a second embodiment of the present invention, the compounds of Formula I are prepared by reacting cyclic amide initiators of Formula IX:

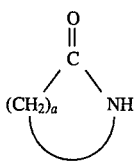

wherein a is as defined hereinbefore, with one or more epoxides. Non-limiting examples of cyclic amides which can be employed include cycloalkyl lactams such as, cyclopropyl lactam, cyclobutyl lactam (butyrolactam), cyclopentyl lactam, cyclohexyl lactam (caprolactam), cycloheptyl lactam and cyclooctyl lactam, with cyclopropyl lactam, cyclobutyl lactam and cyclohexyl lactam being the most preferred. Select cyclic amide initiators are also available commercially, such as, ε-caprolactam (ε-hexanolactam available commercially from Aldrich Chemical Company), 2-pyrrolidinone (pyrrolidone or γ-butyrolactam available commercially from Aldrich Chemical Company) and laurallactam (2-azacyclotridecanone available commercially from Aldrich Chemical Company) with ε-caprolactam and 2-pyrrolidione being the most preferred.

In a third embodiment, the compounds of Formula I are prepared by reacting cyclic amidoalcohol initiators represented by Formula X:

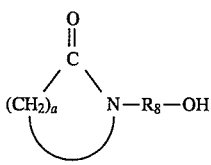

wherein a is as defined hereinabove and $R_8$ is an alkyl group of 2 to 20 carbon atoms. Non-limiting examples of cyclic amidoalcohol initiators which are employed include N-(2-hydroxyethyl)-pyrrolidinone, N-[2-(2-hydroxyethoxy)ethyl] pyrrolidinone N-(2-hydroxypropyl)-pyrrolidinone and N-(2hydroxy-2-methyl-ethyl)-pyrrolidinone, with N-(2-hydroxyethyl)pyrrolidinone being the most preferred.

Select cyclic amidoalcohol initiators are available commercially, such as, N-(2-hydroxyethyl)-pyrrolidinone (obtained from International Specialty Products or Aldrich Chemical Company). The cyclic amidoalcohol initiators are also prepared by any of the methods known and described in the art, for example by the method of Puetzer et al in J. Am. Chem. Soc. 74 4959 (1952), by reacting a lactone of Formula XI:

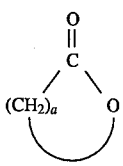

with an aminoalcohol of Formula XII:

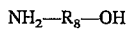

wherein $R_8$ and a are as defined hereinbefore. Illustrative lactones for use in making the cyclic amidoalcohols include: β-propiolactone, γ-caprolactone, β-butyrolactone and δ-valerolactone. Illustrative aminoalcohols for reacting with lactones to make the cyclic amidoalcohol initiators include: 2-amino-1-butanol, 2-(2-aminoethoxy) ethanol, 2-amino-2-ethyl-1,3propanediol, 2-amino-2-methyl-1-propanol, 3-amino-1-propanol and 1-amino-2-propanol.

In a fourth embodiment, the compounds of Formula I are prepared by reacting cyclic amidoalcohol initiators represented by Formula XIII:

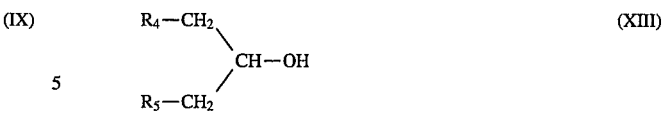

wherein $R_4$ and $R_5$ are as defined hereinbefore with one or more epoxides. Non-limiting examples of the initiators of Formula XII which are employed to prepare the compounds of Formula I include 1,3-bis(pyrrolidinonyl)-propan-2-ol, 1,3-bis(succinimidyl)-propan-2-ol and 1,3-bis(caprolactamyl)-propan-2-ol, with 1,3-bis(pyrrolidinonyl)-propan-2-ol being the most preferred.

The cyclic amidoalcohol initiators may also be prepared by any of the methods known and described in the art. For example, lactones of Formula XIV:

wherein a is as defined hereinbefore, are mixed with diaminoalcohols of Formula XV:

and the mixture is heated to a temperature from about 100° C. to about 250° C. for from 1 to 12 hours. As a result, a 1,3-bis(lactam)propan-2-ol is achieved. Alternatively, the cyclic amidoalcohol initiators may be prepared by mixing a succinic anhydride of Formula XVI:

wherein z is as defined hereinbefore, with the diaminoalcohol of Formula XV and heating the mixture to a temperature from about 100° C. to about 250° C. for from 1 to 12 hours. As a result, a 1,3-bis(imide)propan-2-ol is achieved.

Illustrative lactones for use in making the cyclic amidoalcohols include: β-butyrolactone, δ-valerlactone, γ-caprolactone and β-propiolactone.

Illustrative succinic anhydrides for use in making the cyclic amidoalcohol initiators include: succinic anhydride (available commercially from Aldrich) and glutaric anhydride (available commercially from Aldrich).

Illustrative diaminoalcohols include 1,3-diamino-2-propanol and 3,5-diaminobenzyl alcohol.

In a still additional embodiment, the compounds of Formula I are prepared by reacting an alkyl-phenol wherein the alkyl contains from 1 to 100 carbon atoms with one or more epoxides. Preferably the alkyl-phenol is N-nonylphenol.

The one or more epoxides employed in the reaction with the initiators to prepare the compounds of Formula I contain from 2 to 100 carbon atoms, preferably from 2 to 20 carbon atoms, more preferably from 2 to 4 carbon atoms, and most preferably four carbon atoms. The epoxides are of Formula XVII:

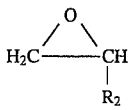

or Formula XVII

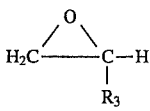

wherein $R_2$ and $R_3$ are as defined hereinbefore.

In one embodiment of the present invention, the epoxides represented by Formula XVII and Formula XVIII in which $R_2$ and $R_3$ are selected from hydrogen and alkyl of 1 to 100 carbon atoms are utilized. Ideally these epoxides are 1,2-epoxyalkanes. Suitable 1,2-epoxyalkanes include 1,2-epoxyethane, 1,2-epoxypropane, 1,2-epoxybutane, 1,2-epoxydecane, 1,2-epoxydodecane, 1,2-epoxyhexadecane, 1,2-epoxyoctadecane and mixtures thereof.

The epoxides employed in the reaction with the above initiators to prepare the compounds of Formula I may also be amide-containing glycidyl ethers such as those represented by Formula XIX:

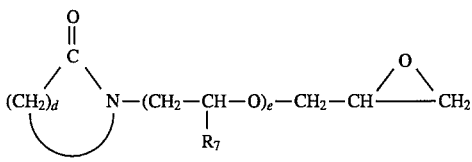

wherein $R_7$, d and e are as defined hereinbefore. Non-limiting examples of the amide-containing glycidyl ethers of Formula XIX which are employed include N-(2,3-epoxypropyl)pyrrolidinone, N(2,3-epoxypropyl)caprolactam and N-(2,3-epoxypropyl) δ-valerolactam.

The amide-containing glycidyl ethers may be prepared by any of the methods known and described in the art, for example, in U.S. Pat. Nos. 4,713,463 and 4,801,400, each incorporated herein by reference. In U.S. Pat. No. 4,713,463, the amide-containing glycidyl ethers are prepared by adding epichlorohydrin to a 2 liter, 4-neck flask equipped with stirrer, reflux condenser, thermometer, and dropping funnel containing a mixture of sodium hydroxide and water while stirring. Tetrabutyl ammonium hydrogen sulfate is then introduced during agitation. The reaction mixture is stirred at room temperature for 15 minutes and the reaction exothermed to about 35° C. To the above reaction mixture a lactam is then added dropwise over a period of two hours. The resulting exothermic reaction is maintained between 35° C.–45° C. using ice water bath. After completion of the lactam addition, the reaction mixture is stirred for an additional 5 hours and filtered and filtrate collected. The precipitated salts is washed with methylene chloride. The filtrate and the methylene chloride washings are combined, dried over anhydrous sodium sulfate and again filtered to remove sodium sulfate. The filtrate is stripped and the residue placed in a distillation flask where, at a temperture of 30° C.–75° C. and about 0.25 mm Hg, the excess epichlorohydrin and the other low-boiling impurities is removed. The desired epoxide product is obtained at 90° C.–95° C. (0.2 mm Hg) and at a yield of 75%. The structure of the product can be confirmed by $^{13}C$ and H NMR data.

In U.S. Pat. No. 4,801,400, the amide-containing glycidyl ethers may be prepared by adding epibromohydrin and ethylene glycol dimethylether to a 5 liter flask equipped with a stirrer, condenser, thermometer and dropping funnel. Potassium pyrrolidone is then added to the mixture over a half hour period of time. The mixture is stirred for 48 hours at 25° C. Potassium bromide is removed by filtration and the product distilled. The fraction boiling at 87° C. to 100° C. at 0.07 to 0.1 mm Hg is collected as 201.8 g of product having a purity of 93% analyzed by gas chromatography.

The epoxides may also be imide-containing glycidyl ethers such as those represented by Formula XX:

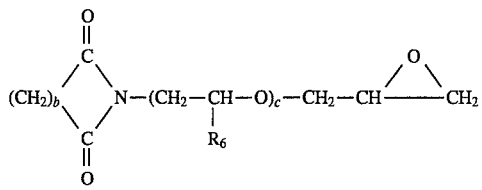

wherein $R_6$, b and c are as defined hereinbefore. Non-limiting examples of the imide-containing glycidyl ethers of Formula XX which are employed include N-(2,3-epoxypropyl)succinimide and N-(2,3-epoxypropyl)glutarimide. The imide-containing glycidyl ethers of Formula XX may be prepared in the same manner as those used to prepare the amide-containing glycidyl ethers of Formula XIX.

In a typical preparation of Formula I compounds, the one or more epoxides are contacted with the initiator at a ratio from about 7:1 to about 55:1 moles of epoxide per mole of initiator. Preferably, they are contacted at a molar ratio from about 10:1 to about 30:1, with the most preferred molar ratio being about 20:1.

The reaction is carried out in the presence of potassium compounds which act as alkoxylation catalysts. Such catalysts are conventional and include potassium methoxide, potassium ethoxide, potassium hydroxide, potassium hydride and potassium-t-butoxide. The preferred catalysts are potassium hydroxide and potassium-t-butoxide. The catalysts are used in a base stable solvent such as alcohol, ether or hydrocarbons. The catalysts are employed in a wide variety of concentrations. Generally, the potassium compounds will be used in an amount from about 0.02% to about 5.0% of the total weight of the mixture, preferably from about 0.1% to about 2.0% of the total weight of the mixture, and most preferably about 0.2% of the total weight of the mixture.

The reaction is conveniently carried out in a conventional autoclave reactor equipped with heating and cooling means. The process is practiced batchwise, continuously or semi-continuously.

The manner in which the alkoxylation reaction is conducted is not critical to the invention. Illustratively, the initiator and potassium compound are mixed and heated under vacuum for a period of at least 30 minutes. The one or more epoxides are then added to the resulting mixture, the reactor sealed and pressurized with nitrogen, and the mixture stirred while the temperature is gradually increased.

The temperature for alkoxylation is from about 80° C. to about 250° C., preferably from about 100° C. to about 150° C., and even more preferably from about 120° C. to about 140° C. The alkoxylation reaction time is generally from about 2 to about 20 hours, although longer or shorter times are employed.

Alkoxylation processes of the above type are known and are described, for example in U.S. Pat. Nos. 4,973,414, 4,883,826, 5,123,932 and 4,612,335, each incorporated herein by reference.

The product of Formula I is normally liquid and is recovered by conventional techniques such as filtration and distillation. The product is used in its crude state or is purified, if desired, by conventional techniques such as aqueous extraction, solid absorption and/or vacuum distillation to remove any remaining impurities.

Other methods for making the compounds of Formula I are known by those skilled in the art. For example, the compounds of Formula I are prepared by reacting an initiator as described hereinbefore with other cyclic ethers. In addition, other catalyst chemistry, such as the use of acidic catalysts, can be employed to achieve the compounds of Formula I.

Fuel Compositions

The compounds of Formula I are useful as additives in fuel compositions which are burned or combusted in internal combustion engines. The fuel compositions of the present invention comprise a major amount of a mixture of hydrocarbons in the gasoline boiling range and a minor amount of one or more of the compounds of Formula I. As used herein, the term "minor amount" means less than about 10% by weight of the total fuel composition, preferably less than about 1% by weight of the total fuel composition and more preferably less than about 0.1% by weight of the total fuel composition.

Suitable liquid hydrocarbon fuels of the gasoline boiling range are mixtures of hydrocarbons having a boiling range of from about 25° C. to about 232° C., and comprise mixtures of saturated hydrocarbons, olefinic hydrocarbons and aromatic hydrocarbons. Preferred are gasoline mixtures having a saturated hydrocarbon content ranging from about 40% to about 80% by volume, an olefinic hydrocarbon content from 0% to about 30% by volume and an aromatic hydrocarbon content from about 10% to about 60% by volume. The base fuel is derived from straight run gasoline, polymer gasoline, natural gasoline, dimer and trimerized olefins, synthetically produced aromatic hydrocarbon mixtures, or from catalytically cracked or thermally cracked petroleum stocks, and mixtures of these. The hydrocarbon composition and octane level of the base fuel are not critical. The octane level, (R+M)/2, will generally be above about 85.

Any conventional motor fuel base can be employed in the practice of the present invention. For example, hydrocarbons in the gasoline can be replaced by up to a substantial amount of conventional alcohols or ethers, conventionally known for use in fuels. The base fuels are desirably substantially free of water since water could impede a smooth combustion.

Normally, the hydrocarbon fuel mixtures to which the invention is applied are substantially lead-free, but may contain minor amounts of blending agents such as methanol, ethanol, ethyl tertiary butyl ether, methyl tertiary butyl ether, and the like, at from about 0.1% by volume to about 15% by volume of the base fuel, although larger amounts may be utilized. The fuels can also contain conventional additives including antioxidants such as phenolics, e.g., 2,6-di-tert-butylphenol or phenylenediamines, e.g., N,N'-di-sec-butyl-p-phenylenediamine, dyes, metal deactivators, dehazers such as polyester-type ethoxylated alkylphenol-formaldehyde resins. Corrosion inhibitors, such as a polyhydric alcohol ester of a succinic acid derivative having on at least one of its alpha-carbon atoms an unsubstituted or substituted aliphatic hydrocarbon group having from 20 to 500 carbon atoms, for example, pentaerythritol diester of polyisobutylene-substituted succinic acid, the polyisobutylene group having an average molecular weight of about 950, in an amount from about 1 ppm by weight to about 1000 ppm by weight, may also be present. The fuels can also contain antiknock compounds such as methyl cyclopentadienylmanganese tricarbonyl and ortho-azidophenol as well as co-antiknock compounds such as benzoyl acetone.

An effective amount of one or more compounds of Formula I are introduced into the combustion zone of the engine in a variety of ways to prevent build-up of deposits, or to accomplish the reduction of intake valve deposits or the modification of existing deposits that are related to octane requirement. As mentioned, a preferred method is to add a minor amount of one or more compounds of Formula I to the fuel. For example, one or more compounds of Formula I are added directly to the fuel or are blended with one or more carriers and/or one or more additional detergents to form an additive concentrate which can be added at a later date to the fuel.

The amount of compound of Formula I used will depend on the particular variation of Formula I used, the engine, the fuel, and the presence or absence of carriers and additional detergents. Generally, each compound of Formula I is added in an amount up to about 1000 ppm by weight, especially from about 1 ppm by weight to about 600 ppm by weight based on the total weight of the fuel composition. Preferably, the amount will be from about 50 ppm by weight to about 400 ppm by weight, and even more preferably from about 75 ppm by weight to about 250 ppm by weight based on the total weight of the fuel composition.

The carrier, when utilized, will have a weight average molecular weight from about 500 to about 5000. Suitable carriers, when utilized, include hydrocarbon based materials such as polyisobutylenes (PIB's), polypropylenes (PP's) and polyalphaolefins (PAO's); polyether based materials such as polybutylene oxides (poly BO's), polypropylene oxides (poly PO's), polyhexadecene oxides (poly HO's) and mixtures thereof (i.e., both (poly BO)+(poly PO) and (poly-BO-PO)); and mineral oils such as Exxon Naphthenic 900 sus and high viscosity index (HVI) oils. The carrier is preferably selected from PIB's, poly BO's, and poly PO's, with poly BO's being the most preferred.

The carrier concentration in the final fuel composition is up to about 1000 ppm by weight. When a carrier is present, the preferred concentration is from about 50 ppm by weight to about 400 ppm by weight, based on the total weight of the fuel composition. Once the carrier is blended with one or more compounds of Formula I, the blend is added directly to the fuel or packaged for future use.

The fuel compositions of the present invention may also contain one or more additional detergents. When additional detergents are utilized, the fuel composition will comprise a mixture of a major amount of hydrocarbons in the gasoline boiling range as described hereinbefore, a minor amount of one or more compounds of Formula I as described hereinbefore and a minor amount of an additional detergent selected from polyalkylenyl amines, Mannich amines, polyalkenyl succinimides, poly(oxyalkylene) carbamates, poly-(alkenyl)-N-substituted carbamates and mixtures thereof. As noted above, a carrier as described hereinbefore may also be included. As used herein, the term "minor amount" means less than about 10% by weight of the total fuel composition, preferably less than about 1% by weight of the total fuel composition and more preferably less than about 0.1% by weight of the total fuel composition.

The polyalkylenyl amine detergents utilized comprise at least one monovalent hydrocarbon group having at least 50 carbon atoms and at least one monovalent hydrocarbon group having at most five carbon atoms bound directly to separate nitrogen atoms of a diamine. Preferred polyalkylenyl amines are polyisobutenyl amines. Polyisobutenyl amines are known in the art and representative examples are disclosed in various U.S. Patents including U.S. Pat. Nos. 3,753,670, 3,756,793, 3,574,576 and 3,438,757, each incorporated herein by reference. Particularly preferred polyisobutenyl amines for use in the present fuel composition include N-polyisobutenyl-N',N'-dimethyl-1,3-diaminopropane (PIB-DAP) and OGA-472 (a polyisobutenyl ethylene diamine available commercially from Oronite).

The Mannich amine detergents utilized comprise a condensation product of a high molecular weight alkyl-substituted hydroxyaromatic compound, an amine which contains an amino group having at least one active hydrogen atom (preferably a polyamine), and an aldehyde. Such Mannich amines are known in the art and are disclosed in U.S. Pat. No. 4,231,759, incorporated herein by reference. Preferably, the Mannich amine is an alkyl substituted Mannich amine.

The polyalkenyl succinimide detergents comprise the reaction product of a dibasic acid anhydride with either a polyoxyalkylene diamine, a hydrocarbyl polyamine or mixtures of both. Typically the succinamide is substituted with the polyalkenyl group but the polyalkenyl group may be found on the polyoxyalkylene diamine or the hydrocarbyl polyamine. Polyalkenyl succinamides are also known in the art and representative examples are disclosed in various U.S. Patents including U.S. Pat. Nos. 4,810,261, 4,852,993, 4,968,321, 4,985,047, 5,061,291 and 5,147,414, each incorporated herein by reference.

The poly(oxyalkylene) carbamate detergents comprise an amine moiety and a poly(oxyalkylene) moiety linked together through a carbamate linkage, i.e.,

$$-O-C(O)-N- \qquad (XXI)$$

These poly(oxyalkylene) carbamates are known in the art and representative examples are disclosed in various U.S. Patents including, U.S. Pat. Nos. 4,191,537, 4,160,648, 4,236,020, 4,270,930, 4,288,612 and 4,881,945, each incorporated herein by reference. Particularly preferred poly(oxyalkylene) carbamates for use in the present fuel composition include OGA-480 (a poly(oxyalkylene) carbamate which is available commercially from Oronite).

The poly(alkenyl)-N-substituted carbamate detergents utilized are of the formula:

$$R-A-\overset{\overset{\displaystyle O}{\|}}{C}-OR^1 \qquad (XXII)$$

in which R is a poly(alkenyl) chain; $R^1$ is a hydrocarbyl or substituted hydrocarbyl group; and A is an N-substituted amino group. Poly(alkenyl)-N-substituted carbamates are known in the art and are disclosed in U.S. Pat. No. 4,936,868, incorporated herein by reference.

The one or more additional detergents are added directly to the hydrocarbons, blended with one or more carriers, blended with one or more compounds of Formula I, or blended with one or more compounds of Formula I and one or more carriers before being added to the hydrocarbons.

The concentration of the one or more additional detergents in the final fuel composition is generally up to about 1000 ppm by weight for each additional detergent. When one or more additional detergents are utilized, the preferred concentration for each additional detergent is from about 50 ppm by weight to about 400 ppm by weight, based on the total weight of the fuel composition, even more preferably from about 75 ppm by weight to about 250 ppm by weight, based on the total weight of the fuel composition.

Engine Tests

Decreasing Intake Valve Deposits

The invention further provides a process for decreasing intake valve deposits in engines utilizing the multiple cyclic nitrogen-containing alkoxylates of the present invention. The process comprises supplying to and combusting or burning in an internal combustion engine a fuel composition comprising a major amount of hydrocarbons in the gasoline boiling range and a minor amount of one or more compounds of Formula I as described hereinbefore.

By supplying to and combusting or burning the fuel composition in an internal combustion engine, deposits in the induction system, particularly deposits on the tulips of the intake valves, are reduced. The reduction is determined by running an engine with clean induction system components and pre-weighed intake valves on dynamometer test stands in such a way as to simulate road operation using a variety of cycles at varying speeds while carefully controlling specific operating parameters. The tests are run for a specific period of time on the fuel composition to be tested. Upon completion of the test, the induction system deposits are visually rated, the valves are reweighed and the weight of the valve deposits is determined.

Controlling Octane Requirement Increases

The invention further provides a process for controlling octane requirement increases in engines utilizing the multiple cyclic nitrogen-containing alkoxylates of the present invention. The process comprises supplying to and combusting or burning in an internal combustion engine a fuel composition comprising a major amount of hydrocarbons in the gasoline boiling range and a minor amount of one or more compounds of Formula I as described hereinbefore.

Octane requirement is the maximum octane number of a gasoline that presents trace knock in a given engine within the engine's normal operating range. An increase in octane requirement is generally experienced during mileage accumulation on a new engine. The increase is typically attributed to an increase in engine deposits. Octane requirement increase control is a performance feature that is usually expressed as a comparison of the octane requirement increase developed with a gasoline containing additives (test gasoline) relative to a version of the same gasoline without additives (base gasoline), i.e., the positive difference obtained by subtracting the results of gasoline containing additives from gasoline which does not contain additives.

The test protocol for octane requirement increase control must establish the stable octane requirement of the base gasoline relative to a clean engine. Base gasoline is typically the test gasoline without additives or special treatment; however, it may be gasoline containing additives for a specific comparison.

Octane requirement increase control testing consists of operating an engine assembled with clean combustion chambers and induction system components on a test gasoline to octane stabilization, measuring the octane requirement at regular intervals. The octane requirement increase control is the difference between the stabilized octane requirement of the engine operated on test gasoline and that of the stabilized octane requirement of the engine on base gasoline.

Reduction of Octane Requirement

The invention still further provides a process for reducing octane requirement in engines utilizing the multiple cyclic nitrogen-containing alkoxylates of the present invention.

The process comprises supplying to and combusting or burning in an internal combustion engine a fuel composition comprising a major amount of hydrocarbons in the gasoline boiling range and a minor amount of one or more compounds of Formula I as described hereinbefore.

Octane requirement reduction is the reduction of the octane requirement of an engine by the action of a particular gasoline, usually measured as a decrease from a stabilized octane requirement condition.

Octane requirement reduction is a performance feature that demonstrates a reduction from the established octane requirement of a base gasoline in a given engine. Octane requirement reduction testing consists of operating an engine, which has achieved stable octane requirement using base gasoline, on a test gasoline for approximately 100 hours. Octane measurements are made daily and octane requirement reduction is a reduction of octane requirement from that of base gasoline. Several octane requirement reduction tests may be conducted in a series for fuel to fuel comparison, or test fuel to base fuel comparison, by restabilizing on base fuel between octane requirement reduction tests.

The contribution of specific deposits is determined by removing deposits of interest and remeasuring octane requirement immediately after the engine is warmed to operating temperature. The octane requirement contribution of the deposit is the difference in ratings before and after deposit removal.

The ranges and limitations provided in the instant specification and claims are those which are believed to particularly point out and distinctly claim the instant invention. It is, however, understood that other ranges and limitations that perform substantially the same function in substantially the same way to obtain the same or substantially the same result are intended to be within the scope of the instant invention as defined by the instant specification and claims.

The invention will be described by the following examples which are provided for illustrative purposes and are not to be construed as limiting the invention.

Examples

Compound Preparation

The multiple cyclic nitrogen-containing alkoxylates used in the following examples were prepared by reacting one or more initiators with one or more epoxides in the presence of a potassium compound to produce compounds of Formula I having a weight average molecular weight (MW) from about 600 to about 4000 as measured by gel permeation chromatography (GPC). Rotary evaporation was typically conducted at a temperature from room temperature to 120° C.

Example 1

Step 1-Preparation of Glycidyl Ether (N-(2,3-epoxypropyl) pyrrolidinone) Epichlorohydrin (329 ml, 4.0 moles), sodium hydroxide (pellets, 160 g, 4.0 moles) and water (16 ml) were added to a two liter, 4-necked flask equipped with stirrer, reflux condenser, thermometer and dropping funnel while stirring. Tetrabutyl ammonium hydrogen sulfate (4.4 g, 0,012 mole) was then introduced during agitation. The resulting mixture was stirred at room temperture for 15 minutes and the reaction exothermed to about 35° C. 2-pyrrolidone (76 ml, 1.0 mole) was then added dropwise over a period of two hours. The resulting exothermic reaction was maintained between 35° C.–45° C. using an ice water bath.

After completion of the 2-pyrrolidone addition, the reaction mixture was stirred for an additional 5 hours before being filtered and the filtrate collected. The precipitated salts were washed with methylene chloride (4×100 mls). The filtrate and the methylene chloride washings were combined, dried over anhydrous sodium sulfate and again filtered to remove sodium sulfate. The filtrate was stripped and the residue (317.1 g) was placed in a distillation flask where, at a temperature of 30° C.–75° C. and about 0.25 mmHg, the excess epichlorohydrin and the other low-boiling impurities were removed. The desired epoxide product was obtained at 90° C.–95° C. (0.2 mm Hg) and in 75% yield. The structure of the compound:

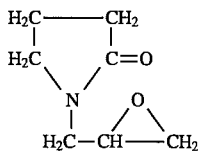

was confirmed by $C^{13}$ and H NMR data.

Step 2-Butoxylation

A mixture of n-nonylphenol (17.5 g, 0.08 mole), potassium hydroxide (0.7 g in 0.7 g water) and toluene (30 g) was subjected to rotary evaporation under reduced pressure. The mixture was charged along with 1,2-epoxybutane (88 g, 1.2 moles), the pyrrolidinone glycidyl ether prepared in Step 1 (22.5 g, 0.16 mole) and toluene (100 g) into a one liter autoclave reactor equipped with a heating device, temperature controller, mechanical stirrer and water cooling system. The autoclave reactor was sealed, purged of air with nitrogen and pressurized to 50 psi with nitrogen at room temperature. The mixture was heated at 131° C.–161° C. for 10 hours. During this time, the pressure ranged from 110 psi to 98 psi. The autoclave reactor was cooled to room temperature and excess gas was vented. The crude product was subjected to rotary evaporation under reduced pressure, extracted with water and rotary evaporation was repeated to achieve a brown liquid final product (58 g). GPC analysis showed MW=909 and a polydispersity of 1.15. IR analysis showed 1680 cm-1 (s) absorption.

Example 2

Step 1-Preparation of 1,3-bis(pyrrolidinonyl)-propan-2-ol

Butyrolactone (95 g, 1.10 moles) and 1,3-diamino-2-propanol (50 g, 0.55 mole) were placed in a 500 ml, 3-necked, round bottom flask equipped with a thermal couple, temperature controller, heating device, nitrogen inlet, stirrer and Dean-Stark Trap. The mixture was heated slowly to 220° C. Water by-product was removed by distillation. After 1 hour of maintaining the temperature at 220° C. to 230° C., GC-MS analysis showed the formation of 1,3-bis(pyrrolidinonyl)-propan-2-ol with a 75% yield.

Step 2-Butoxylation

The initiator of Step 1 (1,3-bis(pyrrolidinonyl)-propan-2ol, 71 g, 0.31 mole) and potassium-t-butoxide (2.3 g) were directly charged along with 1,2-epoxybutane (429 g, 5.96 moles) into a one liter autoclave reactor equipped with a heating device, temperature controller, mechanical stirrer and water cooling system. The autoclave reactor was sealed, purged of air with nitrogen, and pressurized with nitrogen to 50 psi at room temperature. The mixture was heated at 120° C. to 133° C. for 5 hours. The autoclave reactor was then cooled to room temperature and excess gas was vented. The crude product was subjected to rotary evaporation under reduced pressure, extracted with water and rotary evaporation repeated to achieve a dark brown liquid final product (354 g). GPC analysis showed MW=1310 and a polydispersity of 1.18.

Example 3

Step 1-Preparation of Bis-imide Initiator

Succinic anhydride (114.4 g, 1.10 moles) and 1,3-diamino-2-propanol (50 g, 0.55 mole) were placed in a 500 ml, 3-necked, round bottomed flask equipped with a thermal couple, temperature controller, heating device, nitrogen inlet, stirrer and Dean-Stark trap. The mixture was heated slowly to 150° C. Water by-product was removed by distillation. After 1 hour of maintaining the temperature at 150° C.–170° C., GC-MS analysis showed the formation of 1,3-bis(succinimidyl)-propan-2-ol with 80% yield.

Step 2-Butoxylation of Initiator

The initiator of Step 1 (63.5 g, 0.25 mole) and potassium-t-butoxide (2.3 g) were charged along with 1,2-epoxybutane (336.5 g, 4.7 moles) into a one liter autoclave reactor equipped with a heating device, temperature controller, mechanical stirrer and water cooling system. The autoclave reactor was sealed, purged of air with nitrogen, and pressurized with nitrogen to 49 psi at room temperature. The mixture was then heated to 115° C. to 167° C. for 15 hours. During the process, the pressure ranged from 206 psi to 70 psi. The autoclave reactor was cooled to room temperature and excess gas was vented to obtain a crude product. A black liquid final product (357 g) was obtained by removing light material through rotary evaporation under reduced pressure, water extraction and repeating rotary evaporation. GPC analysis showed MW=1300 and a polydispersity of 1.40.

Example 4

A mixture of gamma-caprolactam (28 g, 0.25 mole), potassium hydroxide (1.1 g in 1.0 g water) and toluene (10 g) was subjected to rotary evaporation under reduced pressure to achieve a potassium amide salt. The resulting mixture was charged into a one liter autoclave reactor equipped with a heating device, temperature controller, mechanical stirrer and water cooling system along with 1,2-epoxybutane (356 g, 4.9 moles) and the Initiator of Step 1 of Example 1 (glycidyl ether of pyrrolidinone, 35 g, 0.25 mole). The reactor was sealed, purged of air with nitrogen, and pressurized to 50 psi with nitrogen at room temperature. The mixture was then heated to 115° C. to 131° C. for 11 hours. The autoclave reactor was allowed to cool to room temperature and excess gas was vented. A brown liquid final product was obtained following rotary evaporation under reduced pressure, water extraction and an additional rotary evaporation. GPC analysis showed MW=1200 and a polydispersity of 1.10.

Test Results

In each of the following tests, the base fuel utilized comprised either premium unleaded gasoline (PU) (90+ octane, [R+M/2]) and/or regular unleaded gasoline (RU) (85–88 octane, [R+M/2]). Those skilled in the art will recognize that fuels containing heavy catalytically cracked stocks, such as most regular fuels, are typically more difficult to additize in order to control deposits and effectuate octane requirement reduction and octane requirement increase control. The multiple cyclic nitrogen-containing alkoxylate compounds utilized were prepared as indicated by Example number and were used at the concentration indicated in ppm by weight. The tests employed are described below and the results of the various tests are set forth in the tables below.

Intake Valve Deposit Tests

Engines from vehicles were installed in dynamometer cells in such a way as to simulate road operation using a cycle of idle, low speed and high speed components while carefully controlling specific operating parameters. Fuels with and without the compounds of Formula I were tested 3.3 L Dodges having port fuel injection to determine the effectiveness of the instant compounds in reducing intake valve deposits ("L" refers to liter). Carbureted 0.359 L Honda generator engines were also utilized to determine the effectiveness of the instant compounds in reducing intake valve deposits.

Before each test, the engine was inspected, the induction system components were cleaned and new intake valves were weighed and installed. The oil was changed and new oil and fuel filters, gaskets and spark plugs were installed.

In all engines except the Honda, the tests were run in cycles consisting of idle, 35 mph and 65 mph for a period of 100 hours unless indicated otherwise. In the Honda engines, the tests were run in cycles consisting of a no load idle mode for one minute followed by a three minute mode with a load at 2200 rpm's for a period of 40 hours unless indicated otherwise. At the end of each test, the intake valves were removed and weighed.

All tests of the compounds of the present invention were carried out with additive concentrations (the amount of Compound Example # used) of 200 ppm non-volatile matter (nvm). Base Fuel results which have 0 ppm additive are also included for comparison purposes. The base fuels are indicated by the absence of a Compound Example # (indicated in the Compound Example # column by "- - -").

TABLE 2

| Intake Valve Deposits in Honda Generator Engines | | | | |
|---|---|---|---|---|
| Compound Example # | Engine | Fuel | Conc. ppm by Weight | Avg. Deposit Weight, mg |
| 1 | H2C | RU | 200 | 33.5 |
| — | * | " | 0 | 45.9 |
| 2 | H3C | RU | 200 | 95.7 |
| — | * | " | 0 | 45.9 |
| 3 | H3C | RU | 200 | 130.7 |
| — | * | " | 0 | 45.9 |
| 4 | H3C | RU | 200 | 28.7 |
| — | * | " | 0 | 45.9 |

— Indicates the results achieved with base fuel in the absence of any additive compound (0 ppm additive compound).
*Indicates an average of four test runs in the same base fuel in other Honda generator engines.

TABLE 3

| Intake Valve Deposits in Various Engines | | | | |
|---|---|---|---|---|
| Compound Example # | Engine | Fuel | Conc. ppm By Weight | Avg. Deposit Weight, mg |
| 2 | 3.3 L DODGE | PU | 200 | 519.8 |
| — | " | * | 0 | 196.6 |

— Indicates the results achieved with base fuel in the absence of any additive compound (0 ppm additive compound).
*Indicates an average of three similar premium base fuels in the same engine (3.3 L Dodge).

What is claimed is:

1. A fuel composition comprising a mixture of a major amount of hydrocarbons in the gasoline boiling range and a minor amount of an additive compound having the formula:

$$R_1-(CH_2-CH-O)_x-(CH_2-CH-O)_y H$$
$$\quad\quad\quad\quad | \quad\quad\quad\quad\quad |$$
$$\quad\quad\quad\quad R_2 \quad\quad\quad\quad\quad R_3$$

wherein $R_1$ is selected from the group consisting of alkyl of 1 to 100 carbon atoms, alkyl-phenols wherein the alkyl contains from 1 to 100 carbon atoms, cyclic imides of Formula II:

$$\begin{array}{c} O \\ \| \\ C \\ / \quad \backslash \\ (CH_2)_z \quad\quad N- \\ \backslash \quad / \\ C \\ \| \\ O \end{array} \quad (II)$$

wherein z is from 2 to 20; cyclic amides of Formula III:

$$\begin{array}{c} O \\ \| \\ C \\ / \quad \backslash \\ (CH_2)_a \quad\quad N- \\ \backslash\_\_\_\_/ \end{array} \quad (III)$$

wherein a is from 2 to 20; and cyclic groups of Formula IV:

$$\begin{array}{c} R_4-CH_2 \\ \quad\quad\quad \backslash \\ \quad\quad\quad\quad CH-O- \\ \quad\quad\quad / \\ R_5-CH_2 \end{array} \quad (IV)$$

wherein $R_4$ and $R_5$ are each independently selected from the group consisting of cyclic imides of Formula II and cyclic amides of Formula III;
$R_2$ and $R_3$ are each individually selected from the group consisting of hydrogen, alkyl of 1 to 100 carbon atoms, cyclic imides of Formula V:

$$\begin{array}{c} O \\ \| \\ C \\ / \quad \backslash \\ (CH_2)_b \quad\quad N-(CH_2-CH-O)_c-CH_2- \\ \backslash \quad / \quad\quad\quad\quad\quad\quad | \\ C \quad\quad\quad\quad\quad\quad\quad\quad R_6 \\ \| \\ O \end{array} \quad (V)$$

wherein b is from 2 to 20, each $R_6$ is individually selected from the group consisting of hydrogen and alkyl of 1 to 100 carbon atoms and c is from 0 to 50; and cyclic amides of Formula VI:

$$\begin{array}{c} O \\ \| \\ C \\ / \quad \backslash \\ (CH_2)_d \quad\quad N-(CH_2-CH-O)_e-CH_2- \\ \backslash\_\_\_\_/ \quad\quad\quad\quad\quad | \\ \quad\quad\quad\quad\quad\quad\quad\quad R_7 \end{array} \quad (VI)$$

wherein d is from 2 to 20, each $R_7$ is individually selected from the group consisting of hydrogen and alkyl of 1 to 100 carbon atoms and e is from 0 to 50; x and y are each individually from 1 to 50; and the weight average molecular weight of the additive compound is greater than about 600; with the proviso that at least one of $R_1$, $R_2$ and $R_3$ must be a cyclic amide, a cyclic imide or a cyclic group containing cyclic amides, cyclic imides or a mixture thereof; with the further proviso that $R_1$ must be a cyclic amide of Formula IV when $R_2$ and $R_3$ are hydrogen or alkyl; and with the still further proviso that when only $R_2$ is a cyclic amide of Formula VI or a cyclic imide of Formula V, x must be greater than one; and with the even still further proviso that when only $R_3$ is a cyclic amide of Formula VI or a cyclic imide of Formula V, y must be greater than one.

2. The fuel composition of claim 1 wherein said additive compound is present in an amount from about 50 ppm by weight to about 400 ppm by weight of the fuel composition.

3. The fuel composition of claim 2 wherein the weight average molecular weight of the additive compound is from about 800 to about 4000.

4. The fuel composition of claim 3 wherein $R_2$ and $R_3$ are each individually selected from the group consisting of hydrogen and alkyl of 1 to 20 carbon atoms; x is from 1 to 26 and y is from 1 to 26.

5. The fuel composition of claim 4 wherein $R_2$ and $R_3$ are each individually selected from the group consisting of hydrogen and alkyl of 1 to 2 carbon atoms.

6. The fuel composition of claim 5 wherein $R_1$ is a cyclic group of Formula IV:

$$\begin{array}{c} R_4-CH_2 \\ \quad\quad\quad \backslash \\ \quad\quad\quad\quad CH-O- \\ \quad\quad\quad / \\ R_5-CH_2 \end{array} \quad (IV)$$

wherein $R_4$ and $R_5$ are each cyclic amides of Formula III:

$$\begin{array}{c} O \\ \| \\ C \\ / \quad \backslash \\ (CH_2)_a \quad\quad N- \\ \backslash\_\_\_\_/ \end{array} \quad (III)$$

wherein a is 3 or 5.

7. The fuel composition of claim 5 wherein $R_1$ is a cyclic group of Formula IV:

$$\begin{array}{c} R_4-CH_2 \\ \quad\quad\quad \backslash \\ \quad\quad\quad\quad CH-O- \\ \quad\quad\quad / \\ R_5-CH_2 \end{array} \quad (IV)$$

wherein $R_4$ and $R_5$ are each cyclic imides of Formula II:

$$\begin{array}{c} O \\ \| \\ C \\ / \quad \backslash \\ (CH_2)_z \quad\quad N- \\ \backslash \quad / \\ C \\ \| \\ O \end{array} \quad (II)$$

wherein z is 2 or 3.

8. The fuel composition of claim 5 wherein $R_1$ is a cyclic group of Formula IV:

$$\begin{array}{c} R_4-CH_2 \\ \quad\quad\quad \backslash \\ \quad\quad\quad\quad CH-O- \\ \quad\quad\quad / \\ R_5-CH_2 \end{array} \quad (IV)$$

wherein $R_4$ is cyclic amide of Formula III:

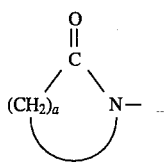 (III)

wherein a is 3 or 5; and $R_5$ is cyclic imide of Formula II:

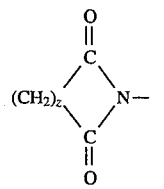 (II)

wherein z is 2 or 3.

9. The fuel composition of claim 3 wherein $R_2$ and $R_3$ are each individually selected from the group consisting of hydrogen, alkyl of 1 to 20 carbon atoms; cyclic imides of Formula V:

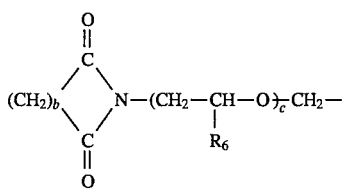 (V)

wherein b is 2, each $R_6$ is individually selected from the group consisting of hydrogen and alkyl of 1 to 20 carbon atoms and c is from 0 to 10; and cyclic amides of Formula VI:

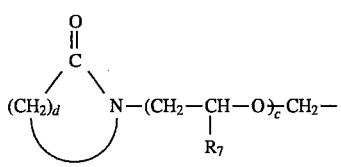 (VI)

wherein d is from 3 to 5, each $R_7$ is individually selected from the group consisting of hydrogen and alkyl of 1 to 20 carbon atoms and e is from 0 to 10; x is from 1 to 26 and y is from 1 to 26.

10. The fuel composition of claim 3 wherein $R_2$ and $R_3$ are each individually selected from the group consisting of hydrogen, alkyl of 1 to 2 carbon atoms; and cyclic amides of Formula VI:

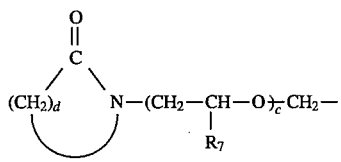 (VI)

wherein d is 3 or 5, each $R_7$ is individually selected from the group consisting of hydrogen and alkyl of 1 to 2 carbon atoms; e is from 0 to 10; x is from 1 to 26 and y is from 1 to 26.

11. The fuel composition of claim 10 wherein $R_1$ is alkyl-phenol comprising nonylphenol; $R_2$ and $R_3$ are each individually selected from the group consisting of alkyl of 2 carbon atoms and cyclic amides of Formula VI wherein e is 0.

12. The fuel composition of claim 10 wherein $R_1$ is cyclic imide of Formula II:

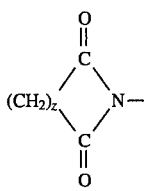 (II)

wherein z is 2 or 3; and $R_2$ and $R_3$ are each individually selected from the group consisting of alkyl of 2 carbon atoms and cyclic amides of Formula VI wherein e is 0.

13. The fuel composition of claim 10 wherein $R_1$ is cyclic amide of Formula III:

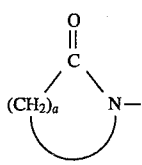 (III)

wherein a is 3 or 5; and $R_2$ and $R_3$ are each individually selected from the group consisting of alkyl of 2 carbon atoms and cyclic amides of Formula VI wherein e is 0.

14. A method for decreasing intake valve deposits in an internal combustion engine which comprises burning in said engine a fuel composition comprising a major amount of hydrocarbons in the gasoline boiling range and a minor amount of an additive compound having the formula:

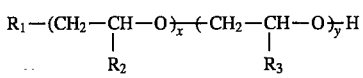

wherein $R_1$ is selected from the group consisting of alkyl of 1 to 100 carbon atoms, alkyl-phenols wherein the alkyl contains from 1 to 100 carbon atoms, cyclic imides of Formula II:

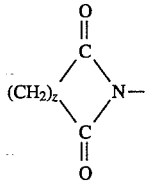 (II)

wherein z is from 2 to 20; cyclic amides of Formula III:

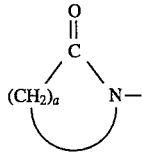 (III)

wherein a is from 2 to 20; and cyclic groups of Formula IV:

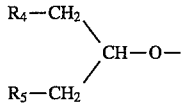 (IV)

wherein $R_4$ and $R_5$ are each independently selected from cyclic imides of Formula II and cyclic amides of Formula III; $R_2$ and $R_3$ are each individually selected from the group consisting of hydrogen, alkyl of 1 to 100 carbon atoms, cyclic imides of Formula V:

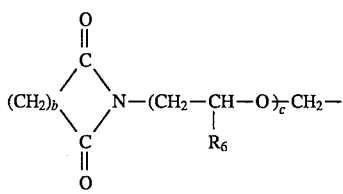
(V)

wherein b is from 2 to 20, each $R_6$ is individually selected from the group consisting of hydrogen and alkyl of 1 to 100 carbon atoms and c is from 0 to 50; and cyclic amides of Formula VI:

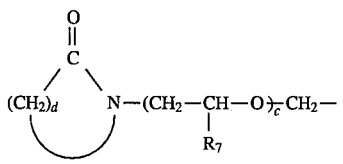
(VI)

wherein d is from 2 to 20, each $R_7$ is individually selected from the group consisting of hydrogen and alkyl of 1 to 100 carbon atoms and e is from 0 to 50; x and y are each individually from 1 to 50; and the weight average molecular weight of the additive compound is greater than about 600; with the proviso that at least one of $R_1$, $R_2$ and $R_3$ must be a cyclic amide, a cyclic imide or a cyclic group containing cyclic amides, cyclic imides or a mixture thereof; with the further proviso that $R_1$ must be a cyclic amide of Formula IV when $R_2$ and $R_3$ are hydrogen or alkyl; and with the still further proviso that when only $R_2$ is a cyclic amide of Formula VI or a cyclic imide of Formula V, x must be greater than one; and with the even still further proviso that when only $R_3$ is a cyclic amide of Formula VI or a cyclic imide of Formula V, y must be greater than one.

15. The method of claim 14 wherein said additive compound is present in an amount from about 50 ppm by weight to about 400 ppm by weight of the fuel composition.

16. The method of claim 15 wherein the weight average molecular weight of the additive compound is from about 800 to about 4000.

17. The method of claim 16 wherein $R_2$ and $R_3$ are each individually selected from the group consisting of hydrogen and alkyl of 1 to 20 carbon atoms; x is from 1 to 26 and y is from 1 to 26.

18. The method of claim 17 wherein $R_2$ and $R_3$ are each individually selected from the group consisting of hydrogen and alkyl of 1 to 2 carbon atoms.

19. The method of claim 18 wherein $R_1$ is a cyclic group of Formula IV:

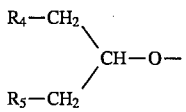
(IV)

wherein $R_4$ and $R_5$ are each cyclic amides of Formula III:

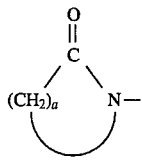
(III)

wherein a is 3 or 5.

20. The method of claim 18 wherein $R_1$ is a cyclic group of Formula IV:

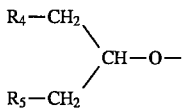
(IV)

wherein $R_4$ and $R_5$ are each cyclic imides of Formula II:

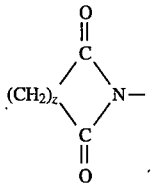
(II)

wherein z is 2 or 3.

21. The method of claim 18 wherein $R_1$ is a cyclic group of Formula IV:

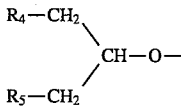
(IV)

wherein $R_4$ is cyclic amide of Formula III:

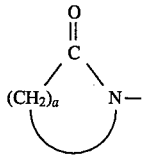
(III)

wherein a is 3 or 5; and $R_5$ is cyclic imide of Formula II:

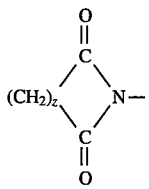
(II)

wherein z is 2 or 3.

22. The method of claim 16 wherein $R_2$ and $R_3$ are each individually selected from the group consisting of hydrogen, alkyl of 1 to 20 carbon atoms; cyclic imides of Formula V:

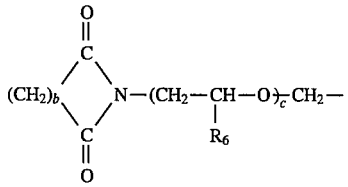
(V)

wherein b is 2, each $R_6$ is individually selected from the group consisting of hydrogen and alkyl of 1 to 20 carbon atoms and c is from 0 to 10; and cyclic amides of Formula VI:

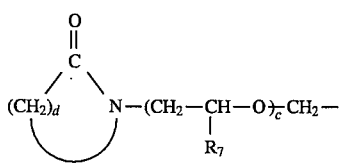
(VI)

wherein d is from 3 to 5, each $R_7$ is individually selected from the group consisting of hydrogen and alkyl of 1 to 20 carbon atoms and e is from 0 to 10; x is from 1 to 26 and y is from 1 to 26.

23. The method of claim 16 wherein $R_2$ and $R_3$ are each individually selected from the group consisting of hydrogen, alkyl of 1 to 2 carbon atoms; and cyclic amides of Formula VI:

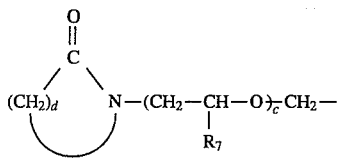

wherein d is 3 or 5, each $R_7$ is individually selected from the group consisting of hydrogen and alkyl of 1 to 2 carbon atoms; e is from 0 to 10; x is from 1 to 26 and y is from 1 to 26.

24. The method of claim 23 wherein $R_1$ is alkyl-phenol comprising nonylphenol; $R_2$ and $R_3$ are each individually selected from the group consisting of alkyl of 2 carbon atoms and cyclic amides of Formula VI wherein e is 0.

25. The method of claim 23 wherein $R_1$ is cyclic imide of Formula II:

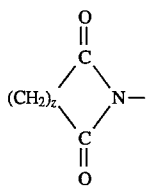

wherein z is 2 or 3; and $R_2$ and $R_3$ are each individually selected from the group consisting of alkyl of 2 carbon atoms and cyclic amides of Formula VI wherein e is 0.

26. The method of claim 23 wherein $R_1$ is cyclic amide of Formula III:

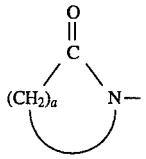

wherein a is 3 or 5; and $R_2$ and $R_3$ are each individually selected from the group consisting of alkyl of 2 carbon atoms and cyclic amides of Formula VI wherein e is 0.

27. A method for controlling octane requirement increase in an internal combustion engine which comprises burning in said engine a fuel composition comprising a major amount of hydrocarbons in the gasoline boiling range and a minor amount of an additive compound having the formula:

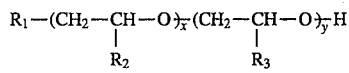

wherein $R_1$ is selected from the group consisting of alkyl of 1 to 100 carbon atoms, alkyl-phenols wherein the alkyl contains from 1 to 100 carbon atoms, cyclic imides of Formula II:

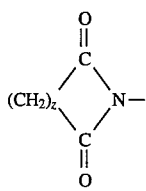

wherein z is from 2 to 20; cyclic amides of Formula III:

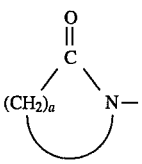

wherein a is from 2 to 20; and cyclic group of Formula IV:

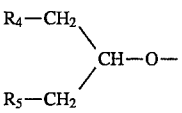

wherein $R_4$ and $R_5$ are each independently selected from the group consisting of cyclic imides of Formula II and cyclic amides of Formula III; $R_2$ and $R_3$ are each individually selected from the group consisting of hydrogen, alkyl of 1 to 100 carbon atoms, cyclic imides of Formula V:

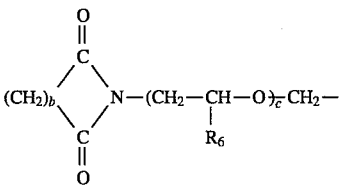

wherein b is from 2 to 20, each $R_6$ is individually selected from the group consisting of hydrogen and alkyl of 1 to 100 carbon atoms and c is from 0 to 50; and cyclic amides of Formula VI:

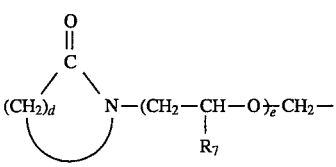

wherein d is from 2 to 20, each $R_7$ is individually selected from the group consisting of hydrogen and alkyl of 1 to 100 carbon atoms and e is from 0 to 50; x and y are each individually from 1 to 50; and the weight average molecular weight of the additive compound is greater than about 600; with the proviso that at least one of $R_1$, $R_2$ and $R_3$ must be a cyclic amide, a cyclic imide or a cyclic group containing cyclic amides, cyclic imides or a mixture thereof; with the further proviso that $R_1$ must be a cyclic amide of Formula IV when $R_2$ and $R_3$ are hydrogen or alkyl; and with the still further proviso that when only $R_2$ is a cyclic amide of Formula VI or a cyclic imide of Formula V, x must be greater than one; and with the even still further proviso that when only $R_3$ is a cyclic amide of Formula VI or a cyclic imide of Formula V, y must be greater than one.

28. A method for reducing octane requirement in an internal combustion engine which comprises burning in said engine a fuel composition comprising a major amount of hydrocarbons in the gasoline boiling range and a minor amount of an additive compound having the formula:

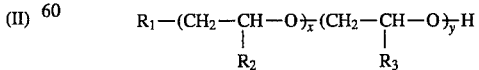

wherein $R_1$ is selected from the group consisting of aklyl of 1 to 100 carbon atoms, alkyl-phenols wherein the alkyl contains from 1 to 100 carbon atoms, cyclic imides of Formula II:

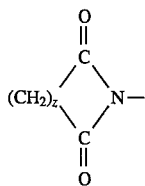

wherein z is from 2 to 20; cyclic amides of Formula III:

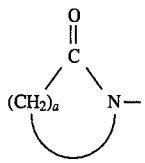

wherein a is from 2 to 20; and cyclic groups of Formula IV:

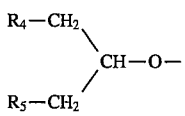

wherein $R_4$ and $R_5$ are each independently selected from the group consisting of cyclic imides of Formula II and cyclic amides of Formula III; $R_2$ and $R_3$ are each individually selected from the group consisting of hydrogen, alkyl of 1 to 100 carbon atoms, cyclic imides of Formula V:

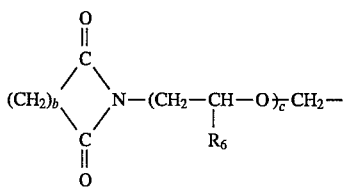

wherein b is from 2 to 20, each $R_6$ is individually selected from the group consisting of hydrogen and alkyl of 1 to 100 carbon atoms and c is from 0 to 50; and cyclic amides of Formula VI:

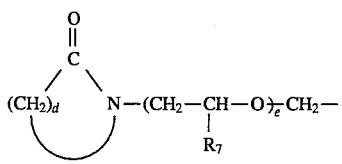

wherein d is from 2 to 20, each $R_7$ is individually selected from the group consisting of hydrogen and alkyl of 1 to 100 carbon atoms and e is from 0 to 50; x and y are each individually from 1 to 50; and the weight average molecular weight of the additive compound is greater than about 600; with the proviso that at least one of $R_1$, $R_2$ and $R_3$ must be a cyclic amide, a cyclic imide or a cyclic group containing cyclic amides, cyclic imides or a mixture thereof; with the further proviso that $R_1$ must be a cyclic amide of Formula IV when $R_2$ and $R_3$ are hydrogen or alkyl; and with the still further proviso that when only $R_2$ is a cyclic amide of Formula VI or a cyclic imide of Formula V, x must be greater than one; and with the even still further proviso that when only $R_3$ is a cyclic amide of Formula VI or a cyclic imide of Formula V, y must be greater than one.

29. A compound having the formula:

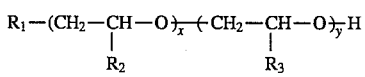

wherein $R_1$ is selected from the group consisting of alkyl of 1 to 100 carbon atoms, cyclic imides of Formula II:

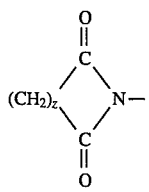

wherein z is from 2 to 20; cyclic amides of Formula III:

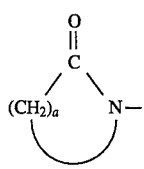

wherein a is from 2 to 20; and cyclic groups of Formula IV:

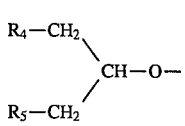

wherein $R_4$ and $R_5$ are each independently selected from the group consisting of cyclic imides of Formula II and cyclic amides of Formula III; $R_2$ and $R_3$ are each individually selected from the group consisting of hydrogen, alkyl of 1 to 100 carbon atoms, cyclic imides of Formula V:**

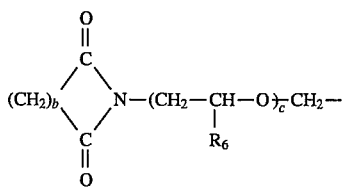

wherein b is from 2 to 20, each $R_6$ is individually selected from the group consisting of hydrogen and alkyl of 1 to 100 carbon atoms and c is from 0 to 50; and cyclic amides of Formula VI:

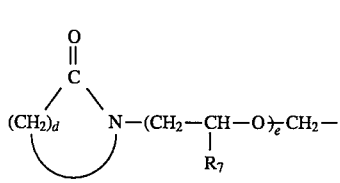

wherein d is from 2 to 20, each $R_7$ is individually selected from the group consisting of hydrogen and alkyl of 1 to 100 carbon atoms and e is from 0 to 50; x and y are each individually from 1 to 50; and the weight average molecular weight of the additive compound is greater than about 600; with the proviso that at least one of $R_1$, $R_2$ and $R_3$ must be a cyclic amide, a cyclic imide or a cyclic group containing cyclic amides, cyclic imides or a mixture thereof; with the further proviso that $R_1$ must be a cyclic amide of Formula IV when $R_2$ and $R_3$ are hydrogen or alkyl; and with the still further proviso that when only $R_2$ is a cyclic amide or a cyclic imide, x must be greater than one; and with the even still further proviso that when only $R_3$ is a cyclic amide or a cyclic imide, y must be greater than one.

30. The compound of claim 29 wherein $R_1$ is a cyclic group of Formula IV wherein $R_4$ and $R_5$ are each cyclic amides of Formula III wherein a is 3; $R_2$ and $R_3$ are each alkyl of 2 carbon atoms; x is from 1 to 26 and y is from 1 to 26.

31. The compound of claim 29 wherein $R_1$ is a cyclic group of Formula IV wherein $R_4$ and $R_5$ are each cyclic imides of Formula II wherein z is 2; $R_2$ and $R_3$ are each alkyl of 2 carbon atoms; x is from 1 to 26 and y is from 1 to 26.

32. The compound of claim 29 wherein $R_1$ is cyclic amide of Formula III wherein a is 5; $R_2$ is alkyl of 2 carbon atoms; $R_3$ is cyclic amide of Formula VI wherein e is 0 and d is 3; x is from 1 to 26 and y is from 1 to 26.

33. A fuel composition comprising a mixture of:

(a) a major amount of hydrocarbons in the gasoline boiling range;

(b) a minor amount of an additive compound having the general formula:

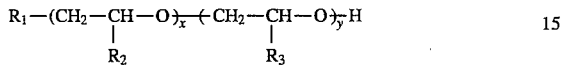

wherein $R_1$ is selected from the group consisting of alkyl of 1 to 100 carbon atoms, alkyl-phenols wherein the alkyl contains from 1 to 100 carbon atoms, cyclic imides of Formula II:

wherein z is from 2 to 20; cyclic amides of Formula III:

wherein a is from 2 to 20; and cyclic groups of Formula IV:

wherein $R_4$ and $R_5$ are each independently selected from the group consisting of cyclic imides of Formula II and cyclic amides of Formula III; $R_2$ and $R_3$ are each individually selected from the group consisting of hydrogen, alkyl of 1 to 100 carbon atoms, cyclic imides of Formula V:

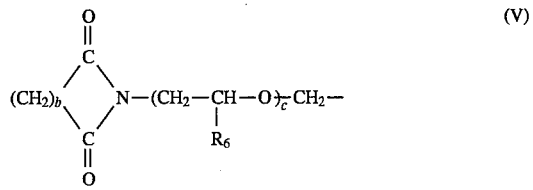

wherein b is from 2 to 20, each $R_6$ is individually selected from the group consisting of hydrogen and alkyl of 1 to 100 carbon atoms and c is from 0 to 50; and cyclic amides of Formula VI:

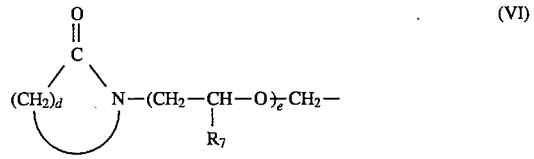

wherein d is from 2 to 20, each $R_7$ is individually selected from the group consisting of hydrogen and alkyl of 1 to 100 carbon atoms and e is from 0 to 50; x and y are each individually from 1 to 50; and the weight average molecular weight of the additive compound is greater than about 600; with the proviso that at least one of $R_1$, $R_2$ and $R_3$ must be a cyclic amide, a cyclic imide or a cyclic group containing cyclic amides, cyclic imides or a mixture thereof; with the further proviso that $R_1$ must be a cyclic amide of Formula IV when $R_2$ and $R_3$ are hydrogen or alkyl; and with the still further proviso that when only $R_2$ is a cyclic amide of Formula VI or a cyclic imide of Formula V, x must be greater than one; and with the even still further proviso that when only $R_3$ is a cyclic amide of Formula VI or a cyclic imide of Formula V, y must be greater than one; and (c) a minor amount of an additional detergent selected from the group consisting of polyalkylenyl amines, mannich amines, polyalkenyl succinamides, poly(oxyalkylene) carbamates, poly(alkenyl)-N-substituted carbamates and mixtures thereof.

* * * * *